United States Patent [19]

Patscot et al.

[11] Patent Number: 5,014,725
[45] Date of Patent: May 14, 1991

[54] DENTAL FLOSS APPLICATOR

[75] Inventors: Linda S. Patscot, 21 October La., Trumbull, Conn.; Harold H. Kawaguchi, Seattle, Wash.

[73] Assignee: Linda S. Patscot, Fairfield, Conn.

[21] Appl. No.: 394,499

[22] Filed: Aug. 14, 1989

[51] Int. Cl.$^5$ .............................................. A61C 15/00
[52] U.S. Cl. .................................... 132/324; 132/323
[58] Field of Search ............... 132/323, 324, 325, 326, 132/327

[56] References Cited

U.S. PATENT DOCUMENTS

| | | | |
|---|---|---|---|
| De. 250,214 | 11/1978 | Chodorow | D28/64 |
| De. 261,566 | 10/1981 | Olson | D28/64 |
| De. 276,942 | 12/1984 | Crews | D28/64 |
| 1,570,357 | 1/1926 | Lawrenz | 132/324 |
| 2,187,899 | 1/1940 | Henne | 132/91 |
| 2,828,754 | 4/1958 | Stewart | 132/323 |
| 2,925,087 | 2/1960 | Kucher | 132/93 |
| 3,918,466 | 11/1975 | Pebbles, Jr. | 132/323 |
| 3,926,201 | 12/1975 | Katz | 132/91 |
| 4,026,308 | 5/1977 | Krivit | 132/91 |
| 4,327,755 | 5/1982 | Endelson | 132/92 R |
| 4,615,349 | 10/1986 | Kukuruzinski | 132/91 |
| 4,807,752 | 2/1989 | Chodorow | 206/63.5 |

*Primary Examiner*—Gene Mancene
*Assistant Examiner*—Michael Lynch
*Attorney, Agent, or Firm*—Kramer, Brufsky & Cifelli

[57] ABSTRACT

An elongated, planar support member is provided with dental floss about its peripheral edge. Multiple notches extending into the support member at various locations about the peripheral edge thereof expose multiple lengths of floss for flossing teeth. The lengths of floss extending across the notches are at various angles with respect to the longitudinal extent of the support member in order that the interdental spaces between various teeth are conveniently and effectively accessed.

Preferably, four lengths of floss are exposed across four notches. Two floss lengths are parallel to a longitudinal axis of the support member and two floss lengths are at an angle to the longitudinal axis of the support member.

The peripheral edge of the support member is provided with a groove. In one embodiment of the invention, the floss is fixed in the groove. In another embodiment, the floss is rotatingly positionable in the groove.

In a disposable embodiment of the invention, the support member is formed of a suitably stiff, hygienic, and moisture resistant material such as impregnated cardboard.

In a nondisposable embodiment of the invention, the support member is formed of a rigid, durable material or a plastic such as polyethylene or nylon.

13 Claims, 3 Drawing Sheets

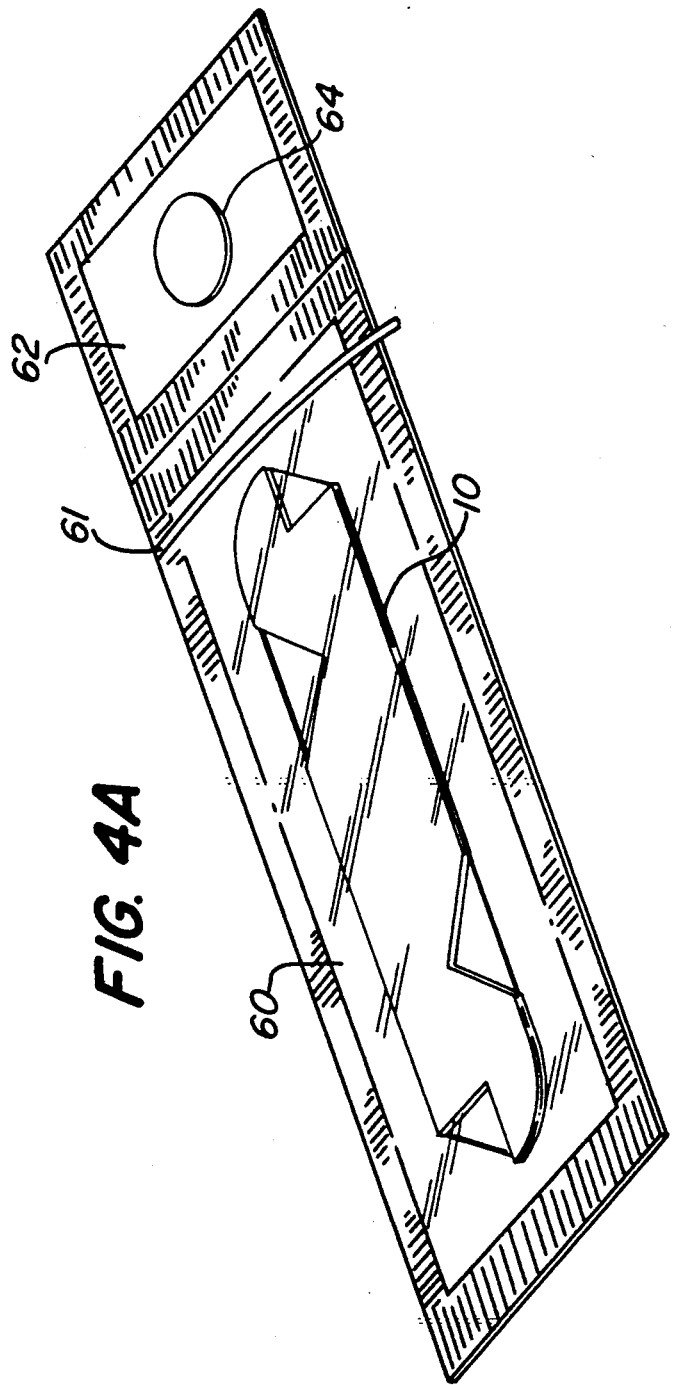

DENTAL FLOSS APPLICATOR

TECHNICAL FIELD OF THE INVENTION

This invention relates to a dental hygiene device and, more particularly, to a dental floss unit for cleaning between the teeth.

BACKGROUND OF THE INVENTION

Interdental cleaning has been a recommended dental health care procedure. Heretofore, however, public places, such as restaurants and the like, have offered only toothpicks to their customers for the purpose of relieving distress caused by food particles lodged between the teeth. Picks of the type offered are generally considered unsatisfactory because they have sharp points which may pierce the gum and may otherwise snap and become lodged between the teeth during the cleaning procedure.

U.S. Pat. No. 2,828,754 to Stewart, entitled "Dental Floss Holder", discloses a dental floss applicator with a limited amount and orientation of exposed floss, making access to certain teeth difficult, and hence ineffective.

U.S. Pat. No. 3,918,466 to Peebles, Jr., entitled "Disposable Dental Cleaning Device", discloses a disposable applicator with a single length of exposed floss, thereby limiting access to certain teeth, making the flossing action difficult and ineffective for certain teeth.

SUMMARY OF THE INVENTION

It is an object of this invention to provide a dental floss applicator that is inexpensive and effective for accessing the full range of teeth.

It is another object of the invention to provide a disposable dental floss applicator.

According to the invention, an elongated, planar support member is provided with dental floss about its perimeter. Multiple notches extending into the support member at various locations about the perimeter thereof expose multiple lengths of floss for flossing teeth. The lengths of floss are at various angles with respect to the longitudinal extent of the support member in order that the interdental spaces between various teeth are conveniently and effectively accessed.

In a described embodiment of the invention, four lengths of floss are exposed, two of which are parallel to a longitudinal axis of the support member, and two of which are at an angle, nominally 45° to the longitudinal axis of the support member.

In one embodiment of the invention, the support member is formed of a suitably stiff, hygienic, and moisture resistant material such as impregnated cardboard. Inasmuch as the dental floss applicator of this invention is intended to be disposable, the support member is preferably biodegradable.

In another embodiment of the invention, the support member is formed of a rigid, durable material such as stainless steel, or a plastic such as polyethylene or nylon.

According to an aspect of the invention, the perimeter (peripheral edge) of the support member is provided with a groove.

In one embodiment of the invention, the floss is fixed about the perimeter of the support member, and the groove aids in stabilizing the floss about the perimeter of the support member. Various techniques for fixing the floss about the perimeter of the support member are disclosed. These include tying the free ends of the floss, gluing the floss at one or more locations about the perimeter of the support member, and inserting the free ends of the floss into retention slits formed in the support member.

In another embodiment of the invention, the floss is rotatingly positionable about the perimeter of the support member, and the groove serves as a guide for the floss. In this manner, "fresh" lengths of floss can be exposed at the notches. According to an aspect of the invention, in this embodiment the free ends of the floss are connected together, such as by gluing or tying, and a tab is provided, preferably at the connection point, for aiding the user in moving the floss from one position to another.

Other objects, features and advantages of the invention will become apparent in light of the following description thereof.

BRIEF DESCRIPTION OF THE DRAWINGS

FIG. 4A is a perspective view of an alternate embodiment of the plastic pack illustrated in FIG. 4.

DETAILED DESCRIPTION OF THE INVENTION

Figure 1:
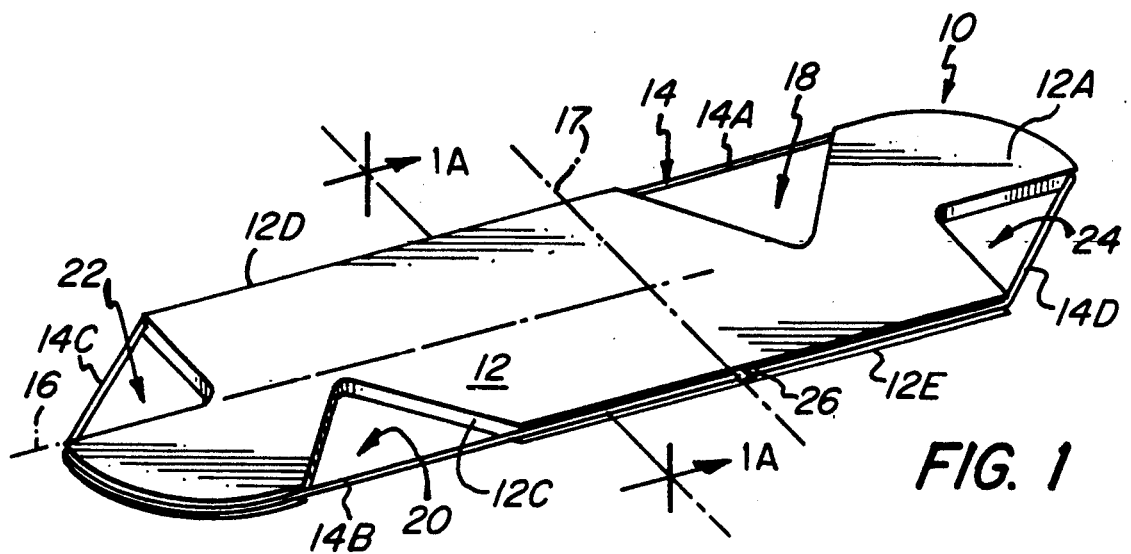
FIG. 1 is a perspective view of the dental floss applicator of this invention.
Figure 1A:
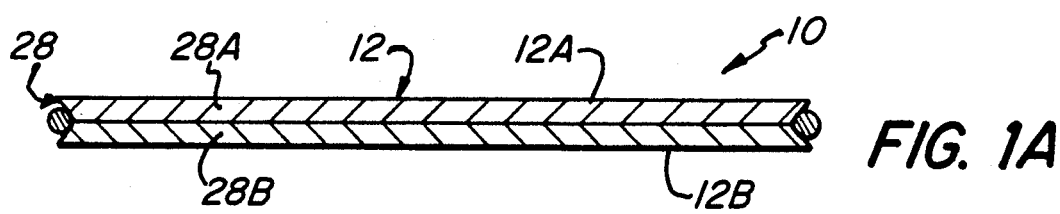
FIG. 1A is a cross-sectional view of the dental floss applicator of FIG. 1, taken on a line A—A therethrough.

FIGS. 1 and 1A show the dental floss applicator 10 of the present invention. The applicator 10 includes a flat, rigid support member 12, discussed in greater detail hereinafter, and a length of dental floss (string) 14 disposed about the perimeter (peripheral edge) of the member 12. As will become evident hereinafter, the member 12 serves to hold the floss 14 in tension and functions as a handle for applying exposed portions of the floss in dental hygiene. The member 12 is also referred to as a "holder" hereinafter.

In plan view, the support member (holder) 12 is seen to be generally rectangular, having a longitudinal axis 16 and a transverse axis 17, a flat upper surface 12A and a flat lower surface 12B. The peripheral edge 12C of the holder 12, as defined by its perimeter, describes a particular geometry that is highly beneficial to the application of the floss 14 for dental hygiene.

More particularly, the holder 12 has a long straight edge 12D on one side, parallel to the longitudinal axis 16 of the holder, and a long straight edge 12E on an opposite side, parallel to the longitudinal axis 16.

Further, the holder 12 is provided with a notch 18 extending into the body of the holder 12 from the one side at one end of the edge 12D, and a notch 20 extending into the body of the holder 12 from the opposite side at one end of the edge 12E longitudinally opposite the one end of the edge 12D. The geometry of the notches 18 and 20 is such that lengths of floss 14A and 14B extend across the notches 18 and 20, respectively, in-line with the edges 12D and 12E, respectively, and parallel to the longitudinal axis of the support member.

Further, the holder 12 is provided with a notch 22 extending into the body of the holder 12 from the one side at an opposite end of the edge 12D, and a notch 24 extending into the body of the holder 12 from the opposite side at an opposite end of the edge 12E. The geometry of the notches 18 and 20 is such that lengths of floss 14C and 14D extend across the notches 22 and 24, respectively, toward the longitudinal axis 16 at an angle with the edges 12D and 12E, respectively, and at an angle to the longitudinal axis of the support member.

As illustrated, the notches 18, 20, 22 and 24 are triangular, but they could be of another configuration such as semicircular.

The ends of the holder 12 are shaped in the following manner. The support member 12 is initially a rectangular structure having a length three to four times greater than its width and having a longitudinal centerline 16. A cut extends into the rectangular structure from one end (previously referred to as the "opposite end") thereof, along the longitudinal centerline, a distance equal to one-half the width thereof. From that point, the cut extends at a right angle to the centerline (i.e. transverse), again one-half the width of the rectangle, to exit at one side of the rectangle. This cut forms the notch 22 in the support member 12, and is preferably formed by stamping. The notch 24 is formed extending inwardly along the centerline from the opposite end (previously referred to as the "one end") of the rectangular structure, one-half the width, and extends at a right angle to exit the opposite side of the support member.

The "un-notched" portion of the one end of the support member is preferably rounded, i.e., forms a quarter-circular arc between the notch 22 and the notch 20. Similarly, the "un-notched" portion of the opposite end of the support member is preferably rounded, i.e., forms a quarter-circular arc between the notches 18 and 24.

The longitudinal and transverse symmetry of the applicator, in other words, the two notches (one straight, one angled) at one end of the applicator "mirror" the two notches at the other end of the applicator, is beneficial in that the flossing motion employed when using one end is identical to the motion employed when using the other end. One could also view this feature as getting "two (applicators) for the price of one."

The straight (i.e., in-line with the edges 12D and 12E) lengths of floss 14A and 14B are particularly well suited for application in dental hygiene to the interdental spaces between incisors and bicuspids. The angled (i.e., at an angle to the edges 12D and 12E) lengths of floss are particularly well suited for application in dental hygiene to the interdental spaces between molars.

The angle of the floss lengths 14C and 14D is shown as 45° with respect to the longitudinal axis, but other suitable angles, for instances between 30°–60°, are of value.

It is within the scope of this invention that dissimilar lengths of floss, such as different thicknesses, span the notches 20 and 22 versus 18 and 24.

As best viewed in FIG. 1, a dollop (bead) of glue 26 secures the free ends of the floss 16 to the edge of the support member 12. It is within the scope of this invention that a portion, or all, of the peripheral edge of the support member, especially adjacent the notches, is treated with an adhesive material, such as a hot melt adhesive, to which the floss adheres (exclusive of the notch areas, of course). The floss would be placed under moderate tension about the peripheral edge, and the support member is brought to an elevated temperature to secure the floss thereto.

As best viewed in FIG. 1A, the peripheral edge of the support member is preferably provided with a groove to stabilize the floss 14 against slipping off of the edge. A v-shaped groove is illustrated. The groove is advantageously formed by two laminates of beveled cardboard 28A and 28B, as shown.

Whether laminated or not, the support member 12 is preferably formed of a suitably stiff, hygienic, and moisture resistant material. In a disposable embodiment, the support member is formed of impregnated cardboard and is preferably biodegradable. In a nondisposable embodiment, the support member is formed of a rigid, durable material such as stainless steel, or a plastic such as polyethylene or nylon.

Advantageously, the flat surface 28A or 28B, or both, of the support member is imprinted with advertising materials (e.g., graphics) and/or instructions for use of the floss applicator. The flat surfaces 28A and 28B also provide easy manipulation of the floss applicator.

Figure 2:
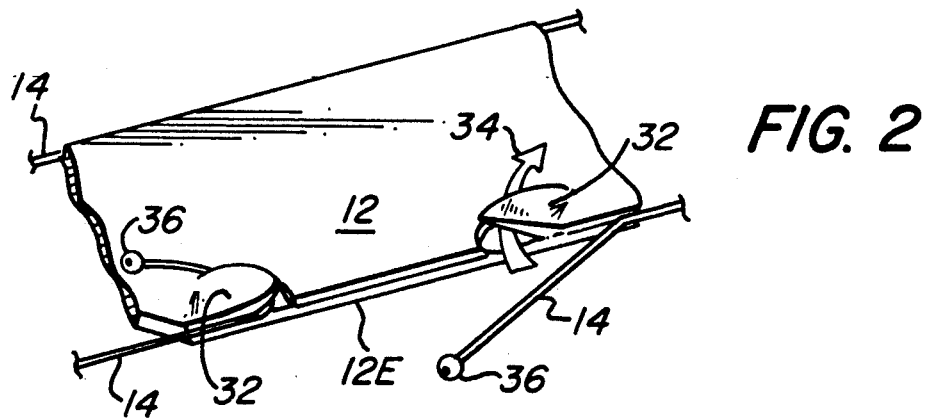
FIG. 2 is a perspective view of an alternate embodiment of the dental floss applicator of this invention.

FIG. 2 shows a central region of an alternate embodiment of the dental floss holder 10 of FIG. 1. Herein, the ends of the floss 14 are not glued together to the periphery of the holder 12. Rather, the peripheral edge 12E of the holder 12 is provided with two "slits" 30 and 32, each for retaining an end of the floss 14. The slits are conveniently formed in one of the laminates (refer to FIG. 1A) in any suitable manner that permits the floss end to be wrapped around (as indicated by the arrow 34 in the slit 32) and retained by the slit. Alternately, the two slits for the floss ends could be formed one in each laminate 28A, 28B. In either case, the tips of the floss ends are conveniently provided with gripping elements, such as are disclosed in U.S. Pat. No. 4,807,752 to Chodorow, entitled "Dental Floss Holders and Package Assembly of Same." The floss retention technique of FIG. 2 is particularly well suited to a nondisposable embodiment of the invention, in which case the support member would periodically be "restrung" with fresh floss.

Figure 3:
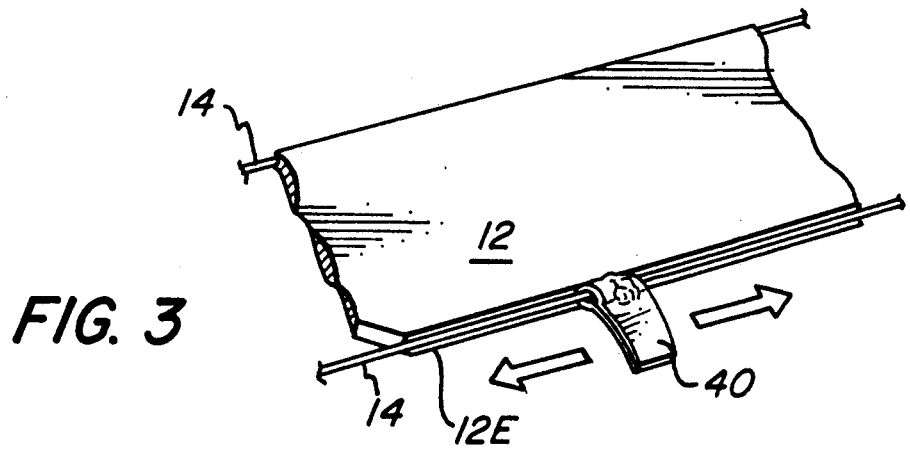
FIG. 3 is a perspective view of an alternate embodiment of the dental floss applicator of this invention.

FIG. 3 shows a central region of an alternate embodiment of the dental floss holder 10 of FIG. 1. In this embodiment, the ends of the dental floss material are glued or tied together independent of the member, and the connection is covered by a tab 40 so that the dental floss can be grasped and moved along the periphery of the member, facilitating multiple use of the floss material in the notched application areas along the periphery of the member.

Figure 4:
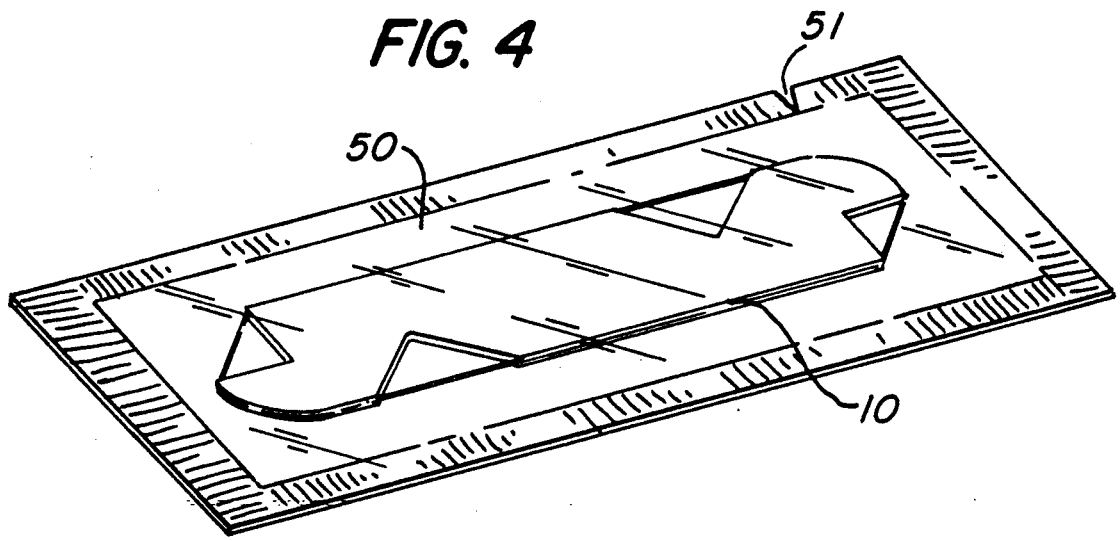
FIG. 4 is a perspective view of the dental floss application of FIG. 1, in a plastic pack.
Figure 5:
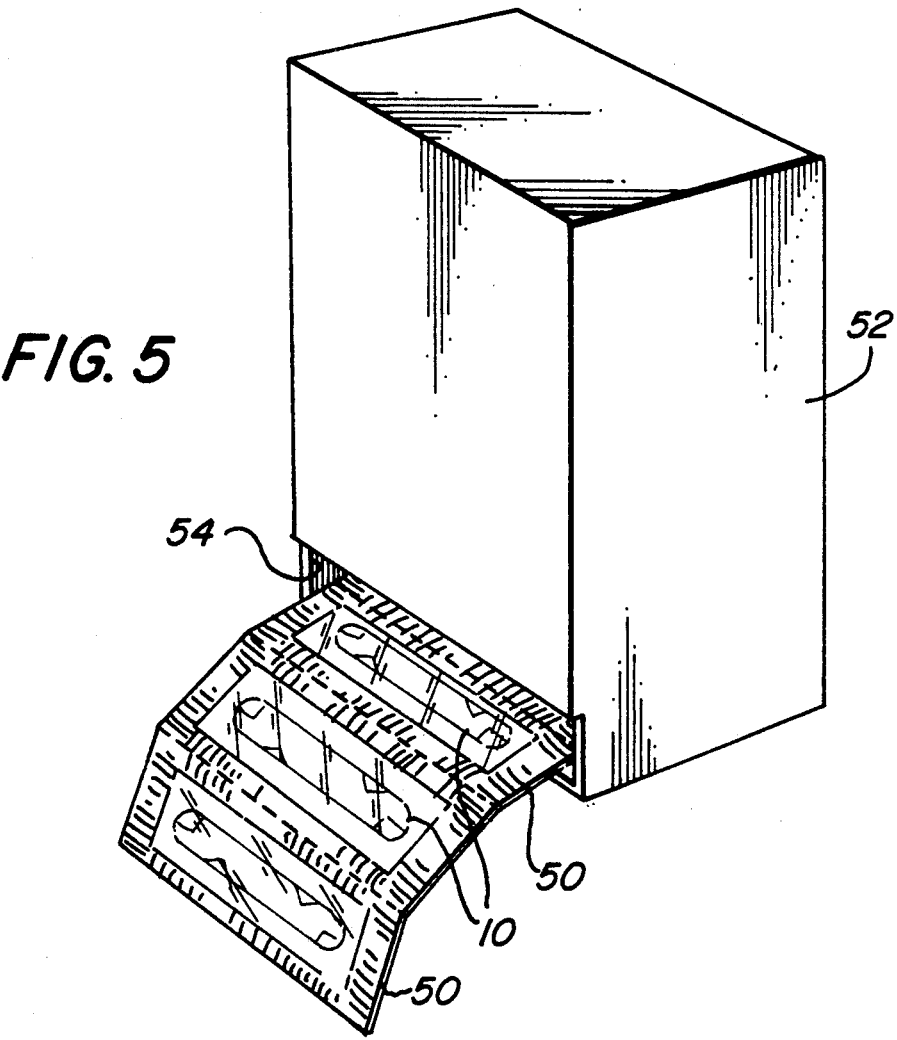
FIG. 5 is a perspective view of a series of plastic packed dental floss applicators, as shown in FIG. 4, in a dispensing unit.

FIGS. 4 and 5 show the dental floss applicator 10 of this invention disposed within plastic packs (sleeves) 50. As best viewed in FIG. 4, each plastic pack is sealed about its periphery in order that the dental floss applicator may be dispensed, such as at a point of sale, in a hygienic manner. As best viewed in FIG. 5, the long edges of a series of plastic packs 50 are joined together to provide a supply of individually packaged dental floss applicators, such as for dispensing in restaurants. In FIG. 5, the series of plastic packs 50 are fanfolded and contained within a suitable container 52 having an opening 54 for dispensing the packaged dental floss applicators.

FIG. 4A shows the dental floss applicator 10 of this invention disposed within an alternate embodiment of the plastic pack. The plastic pack 60 has a separate compartment 62, extending longitudinally from an end thereof, containing a separate dental hygiene article 64. The dental hygiene article 64 is advantageously a mouth freshening and bacteria inhibiting lozenge (as illustrated). This value added accompaniment of a bacterial/mouth freshener inside the sleeve 60 creates a complete "one-stop" oral hygiene "kit".

It should be understood that the lozenge 64 could be disposed within the plastic pack 50 of FIG. 4.

It should be understood that either plastic pack 50 or 60 can be used for sanitary disposal of the dental floss applicator 10, by returning the applicator to within the plastic pack.

It should be understood that the floss is advantageously impregnated with fluoride. As mentioned hereinbefore, the applicator 10 is advantageously provided with two different sizes (diameters) of floss, one size at each end thereof.

It is also advantageous that an opening mechanism be provided for the plastic pack(s). As illustrated in FIG. 4, a notch 51 is provided in a peripheral edge of the plastic pack 50 to facilitate opening thereof. As illustrated in FIG. 4A, a tear strip 61, or string, is provided to facilitate opening the plastic pack 60. Such tear strings are common in adhesive bandage packages.

Thus, the invention provides an inexpensive method of providing an effective dental floss action on all types of teeth types in a convenient and hygienic fashion. Many traditional floss uses require a two-handed applicator that is less convenient and less effective than that achieved with this invention.

What is claimed is:

1. A dental floss applicator comprising:
   an elongated, planar support member having a longitudinal axis and a peripheral edge;
   dental floss disposed about the peripheral edge of the support member;
   at least two notches disposed at one end of the support member and extending into said support member; the floss across one notch extending parallel to the longitudinal axis and the floss across the other notch extending at an angle to the longitudinal axis; and
   at least two notches disposed at the other end of the support number and extending into said support member; the floss across one notch extending parallel to the longitudinal axis and the floss across the other notch extending at an angle to the longitudinal axis.

2. A dental floss applicator according to claim 1, wherein:
   the floss extending across the two notches at one end of the support member forms a mirror image of the floss extending across the other end of the support member.

3. A dental floss applicator according to claim 1, wherein:
   the support member is formed of a suitably stiff, hygienic, and moisture resistant material such as impregnated cardboard.

4. A dental floss applicator according to claim 1, wherein:
   the support member is formed of a rigid, durable material such as stainless steel or plastic.

5. A dental floss applicator according to claim 1, wherein:
   the support member is biodegradable.

6. A dental floss applicator according to claim 1, wherein:
   the dental floss comprises a length of dental floss having free ends which are tied together.

7. A dental floss applicator according to claim 1, wherein:
   the floss is glued at one or more locations about the peripheral edge of the support member.

8. A dental floss applicator according to claim 1, further comprising:
   slits formed in the support member; and wherein the floss comprises a length of dental floss having free ends which are retained by the slits.

9. A dental floss applicator according to claim 8, further comprising:
   gripping elements disposed at the extreme ends of the floss.

10. A dental floss applicator according to claim 1, wherein:
    the peripheral edge of the support member is provided with a groove; and
    the floss is disposed in the groove.

11. A dental floss applicator according to claim 10, wherein:
    the floss is fixed in the peripheral groove of the support member.

12. A dental floss applicator comprising:
    an elongated, planar support member having a longitudinal axis and a peripheral edge, said peripheral edge being provided with a groove;
    dental floss disposed in the groove about the peripheral edge of the support member and rotatingly positionable therein;
    at least two notches disposed at one end of the support member and extending into said support member; the floss across one notch extending parallel to the longitudinal axis and the floss across the other notch extending at an angle to the longitudinal axis; and
    at least two notches disposed at the other end of the support number and extending into said support member; the floss across one notch extending parallel to the longitudinal axis and the floss across the other notch extending at an angle to the longitudinal axis.

13. A dental floss applicator according to claim 12, wherein:
    the floss comprises a length of dental floss having free ends which are secured together at a connection point and a tab is disposed on the floss at the connection point.

* * * * *